United States Patent
Jain et al.

(10) Patent No.: US 11,806,205 B2
(45) Date of Patent: Nov. 7, 2023

(54) OROPHARYNGEAL DAM FOR FACILITATING A SAFE AND EFFICIENT DENTAL TREATMENT

(71) Applicant: Dento Solve LLP, Bangalore (IN)

(72) Inventors: Neha Jain, Bangalore (IN); Shrikanth Sali, Bangalore (IN); Jitendra Kumar, Bangalore (IN)

(73) Assignee: Dento Solve LLP

( * ) Notice: Subject to any disclaimer, the term of this patent is extended or adjusted under 35 U.S.C. 154(b) by 0 days.

(21) Appl. No.: 17/726,597

(22) Filed: Apr. 22, 2022

(65) Prior Publication Data

US 2022/0338956 A1 Oct. 27, 2022

(51) Int. Cl.
- A61C 5/90 (2017.01)
- A61B 1/247 (2006.01)
- A61C 17/10 (2006.01)

(52) U.S. Cl.
CPC .......... *A61C 5/90* (2017.02); *A61B 1/247* (2013.01); *A61C 17/10* (2019.05)

(58) Field of Classification Search
CPC ............ A61C 5/90; A61C 17/10; A61B 1/247
See application file for complete search history.

(56) References Cited

U.S. PATENT DOCUMENTS

| | | | |
|---|---|---|---|
| 2,823,455 A * | 2/1958 | Sprague | A61C 17/08 433/140 |
| 4,053,984 A * | 10/1977 | Moss | A61C 17/10 433/140 |
| 4,204,329 A * | 5/1980 | Kahn | A61C 5/82 433/136 |
| 6,267,591 B1 | 7/2001 | Barstow | |
| 8,303,305 B2 | 11/2012 | Sabbagh | |
| 10,307,049 B2 * | 6/2019 | Hines | A61B 1/24 |
| 2006/0234187 A1 * | 10/2006 | Kilcher | A61C 5/90 433/140 |
| 2007/0148619 A1 * | 6/2007 | Anderson | A61C 17/08 433/136 |
| 2008/0064001 A1 * | 3/2008 | Dorfman | A61C 5/90 433/140 |
| 2009/0035718 A1 * | 2/2009 | Coffee | A61C 17/10 433/93 |

(Continued)

FOREIGN PATENT DOCUMENTS

| | | |
|---|---|---|
| CN | 113476003 A | 10/2021 |
| EP | 3930621 A1 | 1/2022 |

*Primary Examiner* — Ralph A Lewis
(74) *Attorney, Agent, or Firm* — Jason C. Cameron (57) ABSTRACT

An oropharyngeal dam for facilitating a safe and efficient dental treatment is disclosed. The oropharyngeal dam includes a pair of cheek retractors including an upper retractor component, a lower retractor component and a cheek retracting sheet. Further, the upper retractor component, the lower retractor component, the cheek retracting sheet, and a set of lip retractors are collectively configured to retract cheeks of a patient. The oropharyngeal dam includes a tongue protector including an upper protector component, a lower protector component and a tongue protecting sheet. Furthermore, the upper protector component, the lower protector component and the tongue protecting sheet are collectively configured to shield and retract a tongue of the patient. The set of lip retractors are configured to aid lip retraction when pulled outside the mouth.

8 Claims, 12 Drawing Sheets

(56) References Cited

U.S. PATENT DOCUMENTS

| | | | |
|---|---|---|---|
| 2009/0081611 A1* | 3/2009 | Hines | A61C 17/14 |
| | | | 433/140 |
| 2015/0140506 A1* | 5/2015 | Motamedi | A61C 5/90 |
| | | | 433/140 |
| 2016/0008094 A1* | 1/2016 | Jessop | A61B 17/0293 |
| | | | 433/140 |
| 2020/0375696 A1* | 12/2020 | Jessop | A61B 1/24 |

* cited by examiner

OROPHARYNGEAL DAM FOR FACILITATING A SAFE AND EFFICIENT DENTAL TREATMENT

EARLIEST PRIORITY DATE

This Application claims priority from a Provisional patent application filed in India having Patent Application No. 202141012903, filed on Apr. 24, 2021, and titled "ORAL DEVICE FOR SAFE & EFFICIENT DENTAL TREATMENT".

FIELD OF INVENTION

Embodiments of a present disclosure relates to an oral device for dental treatment and more particularly relates to the oropharyngeal dam for facilitating a safe and efficient dental treatment.

BACKGROUND

Prevention of disease transmission has become ever so important where the entire globe is taken off guard by the COVID 19 pandemic. Every moment, bacteria and viruses are transmitted between people, be it at work, at home or in the community. Oral cavity fluids like saliva, blood and nasopharynx host an enormous number of the microorganisms and dental procedures aerosolize blood and saliva all around operatory. This increases the risk of communicable disease transmission by multiple folds, such as Tuberculosis (TB), COVID 19 and the like. Due to the unique nature of dental practice, most dental procedures generate significant amounts of droplets and aerosols, posing potential risks of the communicable disease transmission, such as exaggerated during the COVID 19 Pandemic. Further, aerosol transmission occurs when there is an exposure to high concentrations of the aerosols in a relatively closed environment like in a dental set up. Routine dental procedures generate the aerosols, which pose potential risks not only to the dental care personnel but also to patients.

Furter, indirect evidence suggests that dentists have increased levels of antibodies to a number of viruses when compared to normal population validating the fact that dentists are at high risk of being infected and transmitting these grave diseases. The universal rules post COVID 19, including social distancing and wearing a mouth mask, both are impossible to achieve on a patient at a dental chair. Prevention of formation of bioaerosols and avoiding exposure to the patient's respiratory droplets are crucial not just to protect the dentist but also dental assistant, clinic working area and next patient who will be treated in a same or adjacent operating area.

Existing solutions to prevent formation of the bioaerosols and to maintain asepsis in the operating area, are using additional equipment other than personal protective equipment to minimize cross contamination during dental procedure, such as a dental rubber dam, a cheek and lip retractor, a throat shield, a sweflex saliva ejectors, a svedopter, a dry field system, a mouth prop, a bite block, a isolite, umbrella, hands free suction devices, air filtration systems, an extra oral suction, fogging machines and the like. The use of additional equipment increases cost of operating and decreases capacity of treating more patients up to 30%, as more time, energy and resources are lost in minimising cross contamination and maintaining disinfection. Further, post pandemic, there has been an increase in dental disease burden by 40-60%. As a result, patients have to pay more for the treatments (up to twice the pre pandemic fees) and have to wait longer for dental appointments. The use of additional equipments also increased biomedical waste generation i.e., 46% per day in 2021. Furthermore, most of dental practitioners do not use the dental rubber dam as they find it technique sensitive as it involves multiple steps in application. Also, the dental rubber dam can be used in few dental procedures only and even causes back splatter of the aerosols. The dental rubber dam aid in tooth isolation and throat barrier. However, it fails to provide functions of saliva evacuation, soft tissue retraction and the like. Further, the dental rubber dam doesn't provide anatomically contoured frames, sheet rips easily and taking intra oral radiographs is difficult when the dental rubber dam is placed in the mouth. The dental rubber dam's components can snap in the patient's mouth & there is always a risk of patient swallowing the dental rubber dam components. It can also cause damage to oral soft tissues while placement & removal. Additionally, the dentist faces multiple challenges while performing the dental procedures including but not limited to maintaining a dry working field, evacuation of all fluids and debris generated during procedure, retracting patient's cheek, keeping the tongue away from the operating area and keeping the patient's mouth open in a comfortable static position, protecting the dental assistant, and minimizing the need for extra assistants.

Other contemporary solutions are available for easing out entire dental treatment process. However, all have certain limitations such as leaving the throat exposed, not assisting in minimizing aerosol-based disease transmission, providing for introduction of multiple devices in the patient's mouth for different functions, no advantage of throat shield, tongue protection, tooth isolation, saliva evacuation, soft tissue retraction and the like. Although, some of the other solutions provide some advantages but are met with other limitations of involving multiple steps in application, and not providing anatomically contoured frames. For example, the cheek and lip retractor provide basic function of soft tissue retraction. However, it doesn't provide the functionality of the throat barrier, the tongue protection, the saliva evacuation, the bite block, and the like. Further, the throat shield doesn't provide the functionality of the tongue protection, the saliva evacuation, the soft tissue retraction, the bite block, and the like. The sweflex saliva ejectors and the svedopter fail to provide the functionality of the cheek and lip retraction, the throat barrier, bite block, and the like. Furthermore, the dry field system fails to provide the functionality of the throat barrier, bite block, and the like. The mouth props and the bite block doesn't provide the functionality of the throat barrier, the saliva evacuation, the cheek and tongue retraction and the like. Further, the isolite allows for working only on one side of the mouth. The umbrella only retracts the lips and tongue. It doesn't provide the functionality of the saliva evacuation, the throat barrier, the bite block and the like.

Hence, there is a need for an oropharyngeal dam for facilitating a safe and efficient dental treatment, in order to address the aforementioned issues.

BRIEF DESCRIPTION

In accordance with one embodiment of the disclosure, an oropharyngeal dam for facilitating a safe and efficient dental treatment is disclosed. The oropharyngeal dam includes a pair of cheek retractors, a set of lip retractors and a tongue protector. Further, the pair of cheek retractors are located between the set of lip retractors. Each of the pair of cheek retractors includes an upper retractor component configured to adapt to soft tissues of a buccal vestibule of upper back teeth. The pair of cheek retractors also include a lower retractor component configured to adapt to a buccal vestibule of a lower back teeth. Furthermore, the pair of cheek retractors include a cheek retracting sheet extending between the upper retractor component and the lower retractor component. The upper retractor component, the lower retractor component, the cheek retracting sheet, and the set of lip retractors are collectively configured to retract cheeks of a patient. The tongue protector is located between the pair of cheek retractors. Further, the tongue protector includes an upper protector component configured to adapt to a palate of mouth. The tongue protector also includes a lower protector component configured to adapt to soft tissues of a lower lingual vestibule. Furthermore, the tongue protector includes a tongue protecting sheet extending between the upper protector component and the lower protector component. The upper protector component, the lower protector component and the tongue protecting sheet are collectively configured to shield and retract a tongue of the patient. The set of lip retractors adjoined with edges of the pair of cheek retractors. The set of lip retractors are configured to aid lip retraction when pulled outside the mouth.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended figures.

BRIEF DESCRIPTION OF THE DRAWINGS

The disclosure will be described and explained with additional specificity and detail with the accompanying figures in which.

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated online platform, and such further applications of the principles of the disclosure as would normally occur to those skilled in the art are to be construed as being within the scope of the present disclosure.

The terms "comprises", "comprising", or any other variations thereof, are intended to cover a non-exclusive inclusion, such that a process or method that comprises a list of steps does not include only those steps but may include other steps not expressly listed or inherent to such a process or method. Similarly, one or more devices or subsystems or elements or structures or components preceded by "comprises . . . a" does not, without more constraints, preclude the existence of other devices, subsystems, elements, structures, components, additional devices, additional subsystems, additional elements, additional structures or additional components. Appearances of the phrase "in an embodiment", "in another embodiment" and similar language throughout this specification may, but not necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

Referring now to the drawings, and more particularly to FIG. 1A through FIG. 2C, where similar reference characters denote corresponding features consistently throughout the figures, there are shown preferred embodiments and these embodiments are described in the context of the following exemplary system and/or method.

In the following specification and the claims, reference will be made to a number of terms, which shall be defined to have the following meanings. The singular forms "a", "an", and "the" include plural references unless the context clearly dictates otherwise.

Figure 1A:
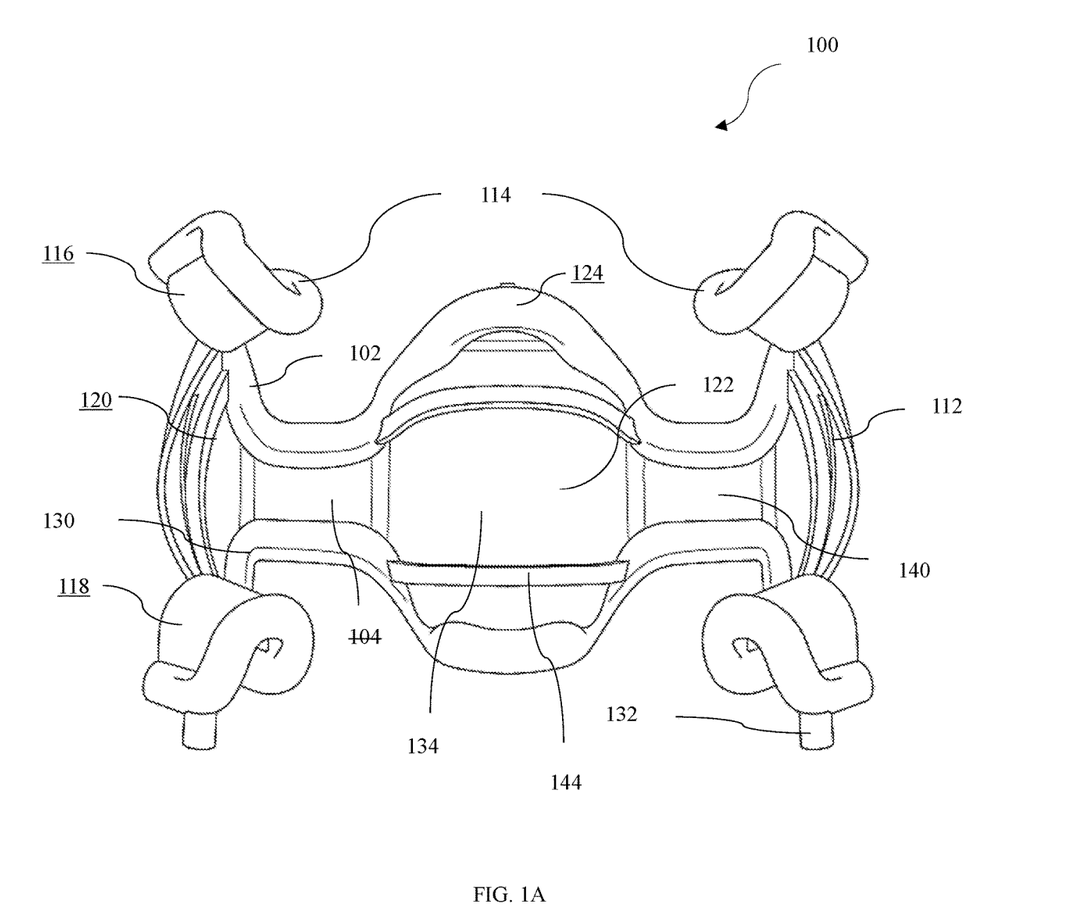
FIG. 1A is a front-view of an exemplary oropharyngeal dam for facilitating a safe and efficient dental treatment, in accordance with an embodiment of the present disclosure.
Figure 1B:
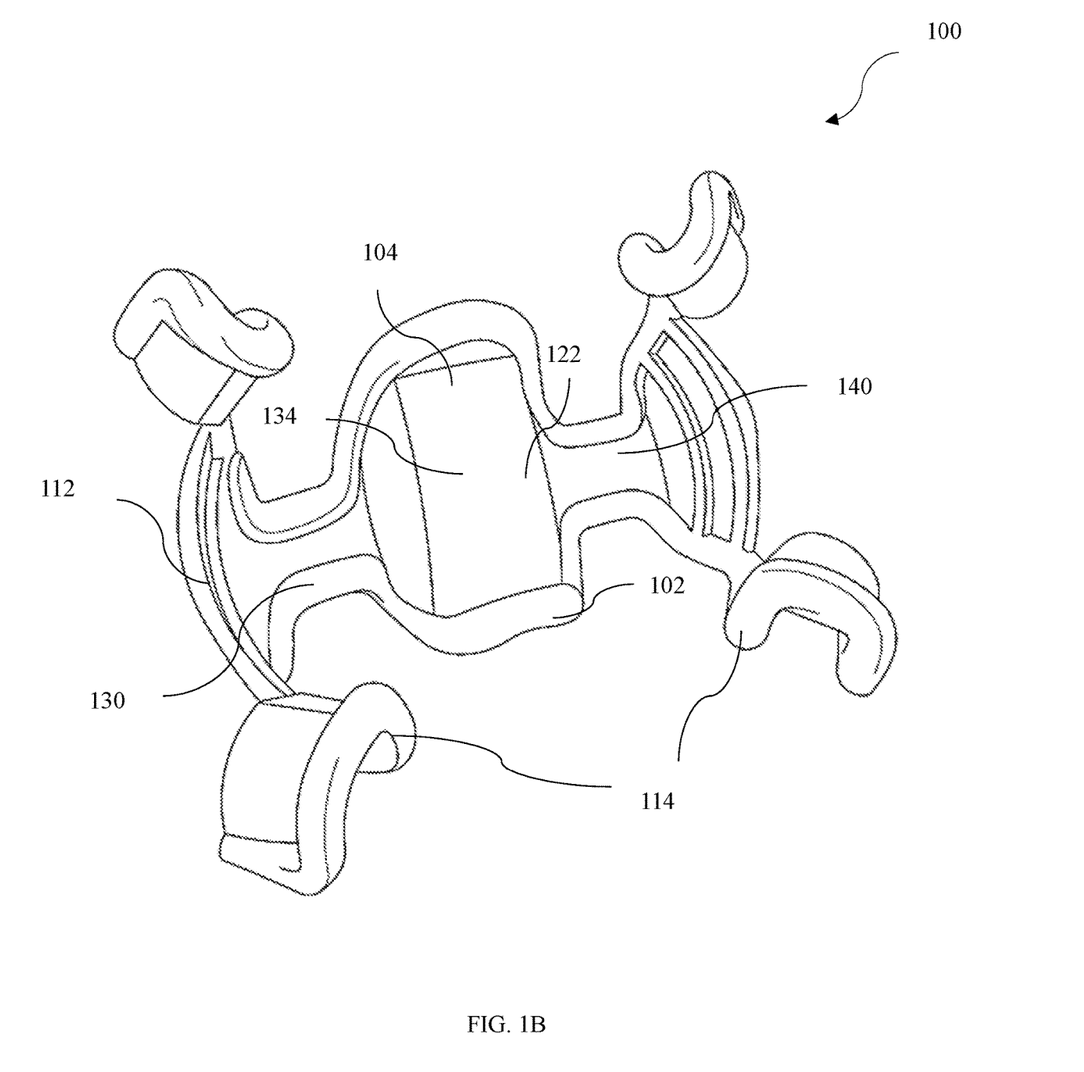
FIG. 1B is a perspective-view of the exemplary oropharyngeal dam for facilitating the safe and efficient dental treatment, in accordance with an embodiment of the present disclosure.

FIG. 1A is a front-view of an exemplary oropharyngeal dam 100 for facilitating a safe and efficient dental treatment, in accordance with an embodiment of the present disclosure. FIG. 1B is a perspective-view of the exemplary oropharyngeal dam 100 for facilitating the safe and efficient dental treatment, in accordance with an embodiment of the present disclosure. For the sake of brevity, FIG. 1A and FIG. 1B have been explained together.

In an embodiment of the present disclosure, the oropharyngeal dam 100 is an intra oral device used by dentists on their patients to minimize cross contamination and enhance safety & efficiency of dental practice. The oropharyngeal dam 100 is made of a frame 102 and a sheet 104, as shown in FIG. 1A and FIG. 1B. In an embodiment of the present disclosure, the frame 102 is an open structure that gives shape and support to the sheet 104. In an exemplary embodiment, sheet 104 is located at centre of the frame 102. Further, the sheet 104 includes an inter oral sheet 106 and an extra oral sheet 108. The inter oral sheet 106 adapts from backside of the frame 102. In an embodiment of the present disclosure, the intra oral sheet 106 includes an occlusal barrier 110 with markings that correlate with individual tooth and isolates only an operating tooth and covers rest of teeth. In an embodiment of the present disclosure, the oropharyngeal dam 100 includes self-retaining cervical rims to aid in retaining the sheet 104 onto the tooth without the need of any external retainers or devices. It is used when aerosol & non-aerosol-based procedures are performed. In an embodiment of the present disclosure, the extra oral sheet 108 forms an external barrier and may be used in conjunction with all aerosols forming equipment or devices. The extra oral sheet 108 snaps fit onto the frame 102 to form the external barrier. In an embodiment of the present disclosure, the frame 102, the oropharyngeal dam 100, or a combination thereof are anatomically contoured, flexible, and compressible. The frame 102 includes an upper frame and a lower frame. Further, the upper frame and the lower frame includes one or more inflatable tubes. The one or more inflatable tubes help in adapting the oropharyngeal dam 100 to vestibule. In an embodiment of the present disclosure, the one or more inflatable tubes makes the oropharyngeal dam 100 universal i.e., one size fits all. Furthermore, the oropharyngeal dam 100 includes one or more vents on the sheet 104 to assist breathing for mouth breathers. In an exemplary embodiment of the present disclosure, the sheet 104 may be lingual sheet surfaces.

The oropharyngeal dam 100 includes a pair of cheek retractors 112 located between a set of lip retractors 114. In an embodiment of the present disclosure, the pair of cheek retractors 112 is an outermost tube of the frame 102. Each of the pair of cheek retractors 112 includes an upper retractor component 116, a lower retractor component 118 and a cheek retracting sheet 120. Further, the upper retractor component 116 is configured to adapt to soft tissues of a buccal vestibule of an upper back teeth. The lower retractor component 118 is configured to adapt to a buccal vestibule of a lower back teeth. Furthermore, the cheek retracting sheet 120 extends between the upper retractor component 116 and the lower retractor component 118. In an embodiment of the present disclosure, the upper retractor component 116, the lower retractor component 118, the cheek retracting sheet 120, and the set of lip retractors 114 are collectively configured to retract cheeks of a patient.

Further, the oropharyngeal dam 100 includes a tongue protector 122 located between the pair of cheek retractors 112. In an embodiment of the present disclosure, the tongue protector 122 is an innermost tube of the frame 102. In an embodiment of the present disclosure, the tongue protector 122 is designed to provide maximum area to operate during a dental procedure. The tongue protector 122 includes an upper protector component 124, a lower protector component 126, and a tongue protecting sheet 128. The upper protector component 124 is configured to adapt to palate of mouth. Furthermore, the lower protector component 126 is configured to adapt to soft tissues of a lower lingual vestibule. The tongue protecting sheet 128 extending between the upper protector component 124 and the lower protector component 126. In an embodiment of the present disclosure, the upper protector component 124, the lower protector component 126 and the tongue protecting sheet 128 are collectively configured to shield and retract a tongue of the patient. In an embodiment of the present disclosure, the upper retractor component 116, the lower retractor component 118, the upper protector component 124, and the lower protector component 126 have a tubular structure.

In an embodiment of the present disclosure, the lower protector component 126 includes one or more suction vents 130 configured to aid in suction and evacuation of saliva, oral fluids and bioaerosols formed during the dental procedure. The one or more suction vents 130 are continuous. Further, the one or more suction vents 130 are located in a lower half of the frame 102. The one or more suction vents 130 are connected to one or more external outlets 132 to perform the evacuation. Furthermore, the one or more suction vents 130 and the one or more external outlets 132 includes one or more anti-retraction valves to prevent backflow and cross contamination. In an embodiment of the present disclosure, the one or more suction vents 130 and the one or more external outlets 132 constantly remove the saliva and blood and prevent mixing with dental drill water to minimize cross-contamination.

Furthermore, the oropharyngeal dam 100 includes the set of lip retractors 114 adjoined with edges of the pair of cheek retractors 112. For example, the set of lip retractors 114 include four lip retractors. In an embodiment of the present disclosure, the set of lip retractors 114 are part of the frame 102 that may be placed outside the mouth. The set of lip retractors 114 are in continuation of the pair of cheek retractors 112. The set of lip retractors 114 are configured to aid lip retraction and cheek retraction when pulled outside the mouth.

In an embodiment of the present disclosure, the oropharyngeal dam 100 includes a throat shield 134 located between the upper protector component 124 and the lower protector component 126. In an embodiment of the present disclosure, a barrier running between the upper protector component 124 and the lower protector component 126 forms the throat shield 134. The throat shield 134 has a curved structure. In an embodiment of the present disclosure, the throat shield 134 is a double sheet barrier including an outer sheet 136 and an inner sheet 138. The inner sheet 138 facing towards throat of the patient forms a mechanical barrier to prevent bioaerosol transmission and aspiration of materials used during the dental procedure. Further, the outer sheet 136 facing outwards towards the mouth comprises a set of perforations. The set of perforations collects aerosols of the patient formed during the dental procedure and evacuates the collected aerosols via the one or more suction vents 130. In an embodiment of the present disclosure, the set of perforation are connected to the one or more suction vents 130 present on the lower protector component 126.

Further, the oropharyngeal dam 100 includes a pair of bite blocks 140 located between the pair of cheek retractors 112 and the tongue protector 122. The pair of bite blocks 140 are configured to keep the mouth open in a comfortable and static position throughout the dental procedure. In an embodiment of the present disclosure, a cheek retractor frame and a tongue protector 122 frame meet at the pair of bite blocks 140. The cheek retractor frame and the tongue protector 122 frame are part of the frame 102. The pair of bite blocks 140 are designed, such that they do not cause any gag reflex for the patient. In an embodiment of the present disclosure, the cheek retractor frame includes an extra oral frame 142. The extra oral frame 142 is an outward extension of the cheek retractor frame. Further, the extra oral frame 142 includes a set of attachment studs that aid in retaining the sheet 104 to the frame 102.

In an embodiment of the present disclosure, the oropharyngeal dam 100 includes one or more removable illuminating devices attached to the pair of cheek retractors 112. In an exemplary embodiment of the present disclosure, the one or more removable illuminating devices include one or more Light Emitting Diodes LED(s), fluorescent dyes and the like. Further, the oropharyngeal dam 100 includes one or more flexible straps 144 affixed on the throat shield 134 to hold one or more intra oral pre-operative radiographs, X ray and the like, during the dental procedure.

Further, the oropharyngeal dam 100 includes a flexible mirror placed within or attached to the pair of cheek retractors 112 via a set of straps. In an embodiment of the present disclosure, the flexible mirror is rotated, flexed inward towards the mouth or a combination thereof to visualise an operating area during the dental procedure. The flexible mirror also aids in illumination by reflecting a dental chair light.

In an embodiment of the present disclosure, the oropharyngeal dam 100 is a dark-colored device which also acts as a contrastor for photography and eases the documentation.

Figure 2A:
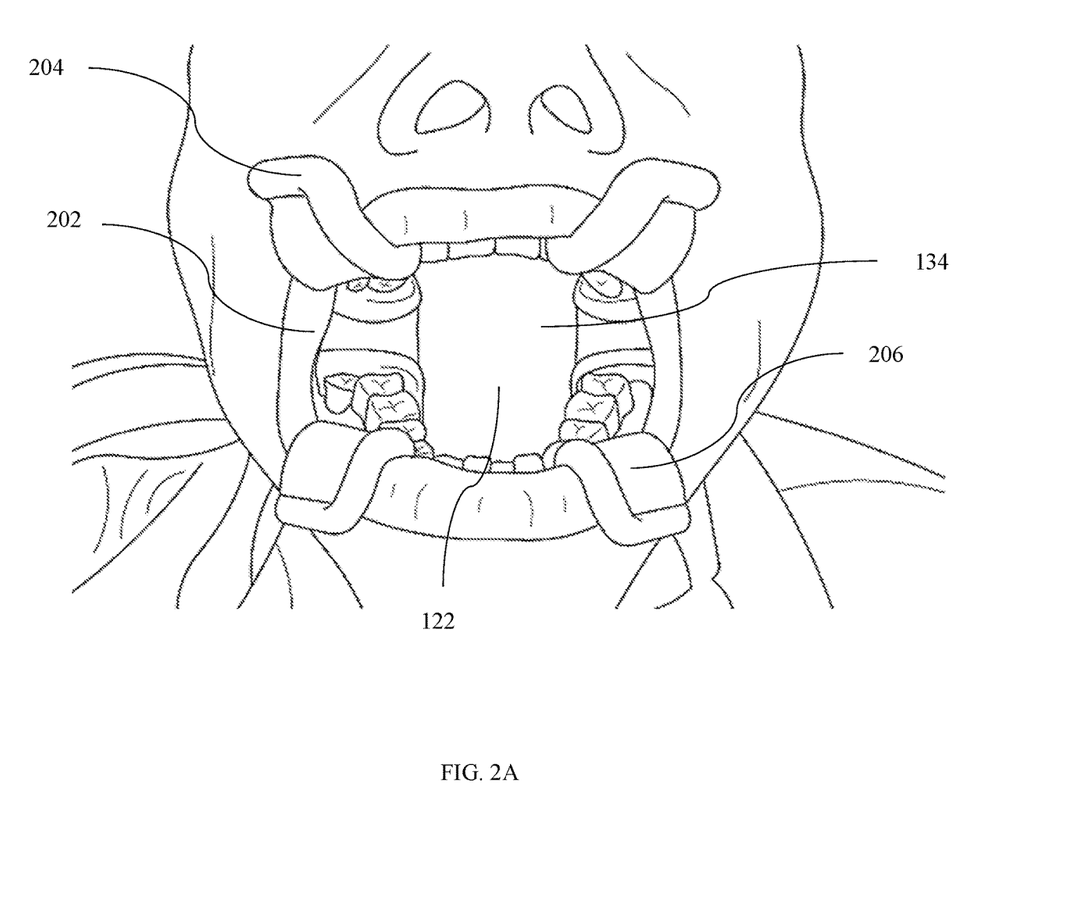
FIG. 2A is a front-view of the exemplary oropharyngeal dam inside a patient's mouth, in accordance with an embodiment of the present disclosure.
Figure 2B:
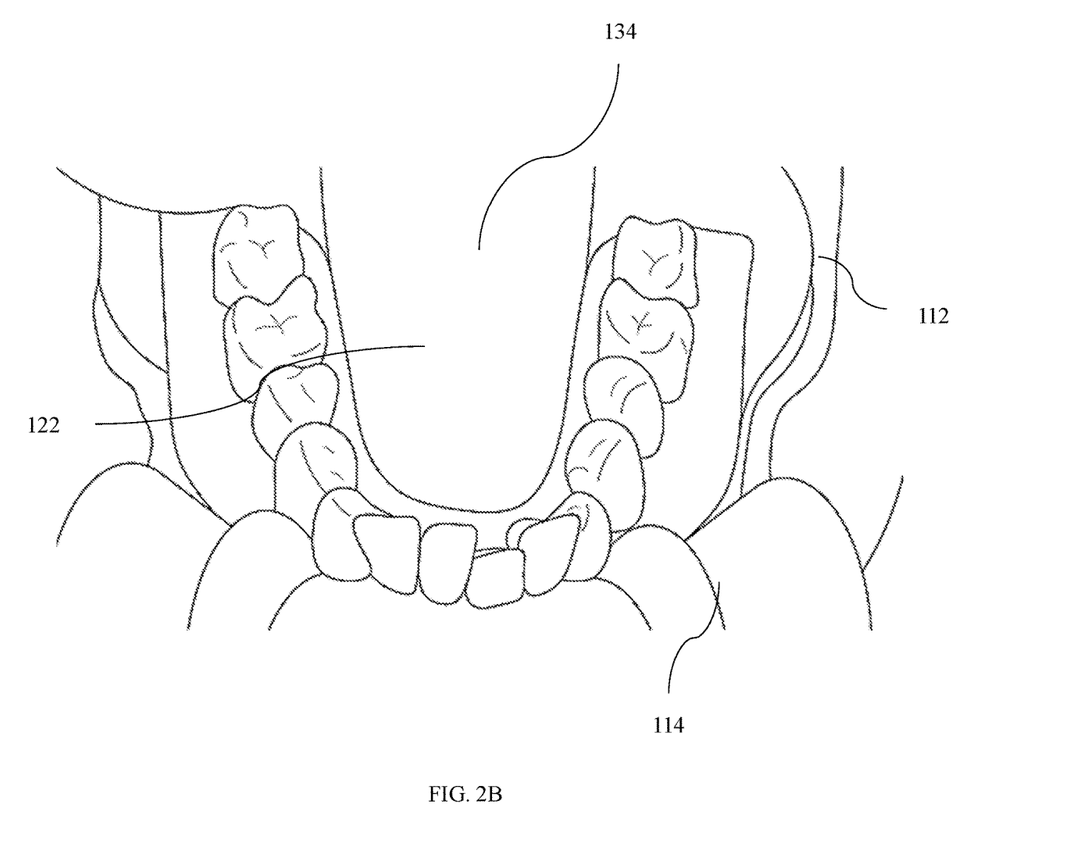
FIG. 2B is a front-view of the exemplary oropharyngeal dam inside the patient's mouth, in accordance with another embodiment of the present disclosure.
Figure 2C:
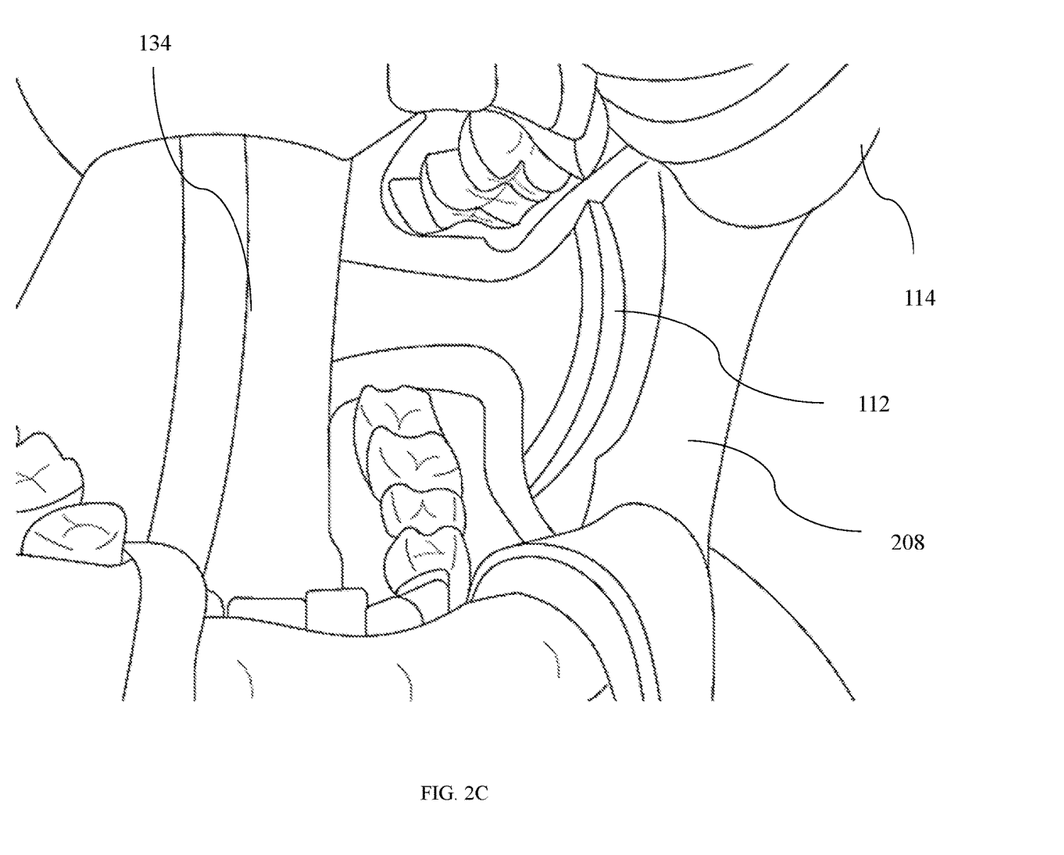
FIG. 2C is a perspective-view of the exemplary oropharyngeal dam inside the patient's mouth, in accordance with an embodiment of the present disclosure.

FIG. 2A is a front-view of the exemplary oropharyngeal dam 100 inside a patient's mouth, in accordance with an embodiment of the present disclosure. Further, FIG. 2B is a front-view of the exemplary oropharyngeal dam 100 inside the patient's mouth, in accordance with another embodiment of the present disclosure. FIG. 2C is a perspective-view of the exemplary oropharyngeal dam 100 inside the patient's mouth, in accordance with an embodiment of the present disclosure. For the sake of brevity, FIGS. 2A-2C have been explained together.

The set of lip retractors 114 retract the lips 202, as shown in FIG. 2A. The set of lip retractors 114 include a pair of upper lip retractors 204 and a pair of lower lip retractors 206. Further, the pair of upper lip retractors 204 retract an upper lip, and the pair of lower lip retractors 206 retract a lower lip, as shown in FIG. 2A. Further, the throat shield 134 and the tongue protector 122 form a throat barrier shielding the tongue and the throat of the patient, as shown in FIGS. 2A-2C.

Further, the set of lip retractors 114 and the pair of cheek retractors 112 collectively facilitates in retraction of the cheeks 208 and the lips 202, as shown in FIG. 2B. Furthermore, the pair of cheek retractor pushes the cheeks 208 from inside the mouth to retract the cheeks 208, as shown in FIG. 2C.

Figure 3:
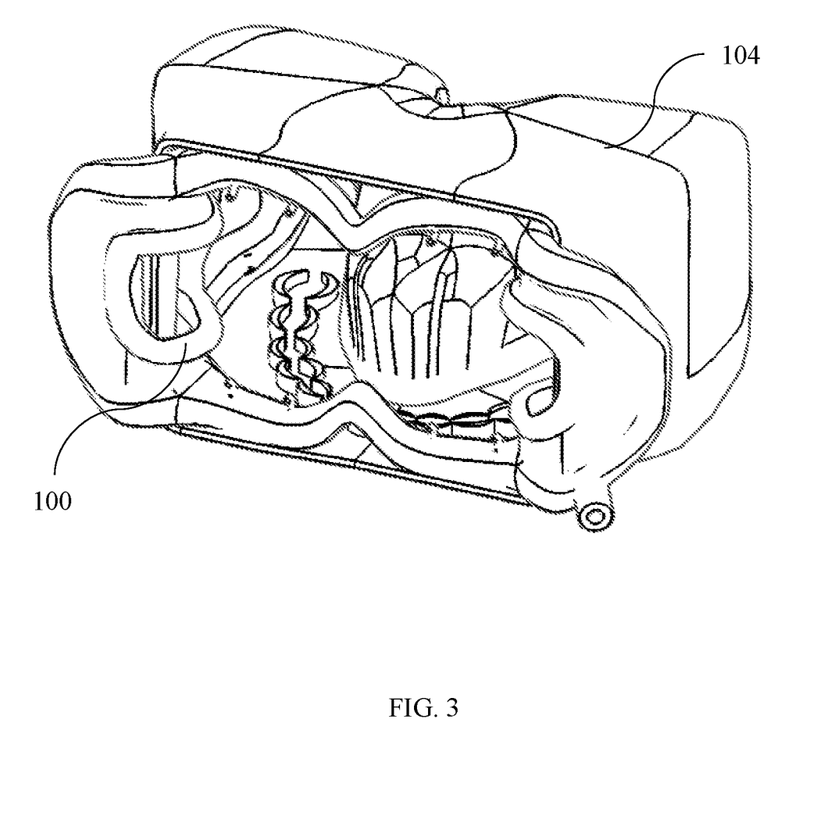
FIG. 3 is a perspective-view of the exemplary oropharyngeal dam, comprising of an exemplary sheet, in accordance with an embodiment of the present disclosure.

FIG. 3 is a perspective-view of the exemplary oropharyngeal dam, comprising of a sheet 104, in accordance with an embodiment of the present disclosure. The sheet 104 can be attached to the exemplary oropharyngeal dam 100 for single or multiple tooth isolation, accurate restorative and endodontic procedures, and to prevent gingival fluid from seeping into the operating site.

Figure 4:
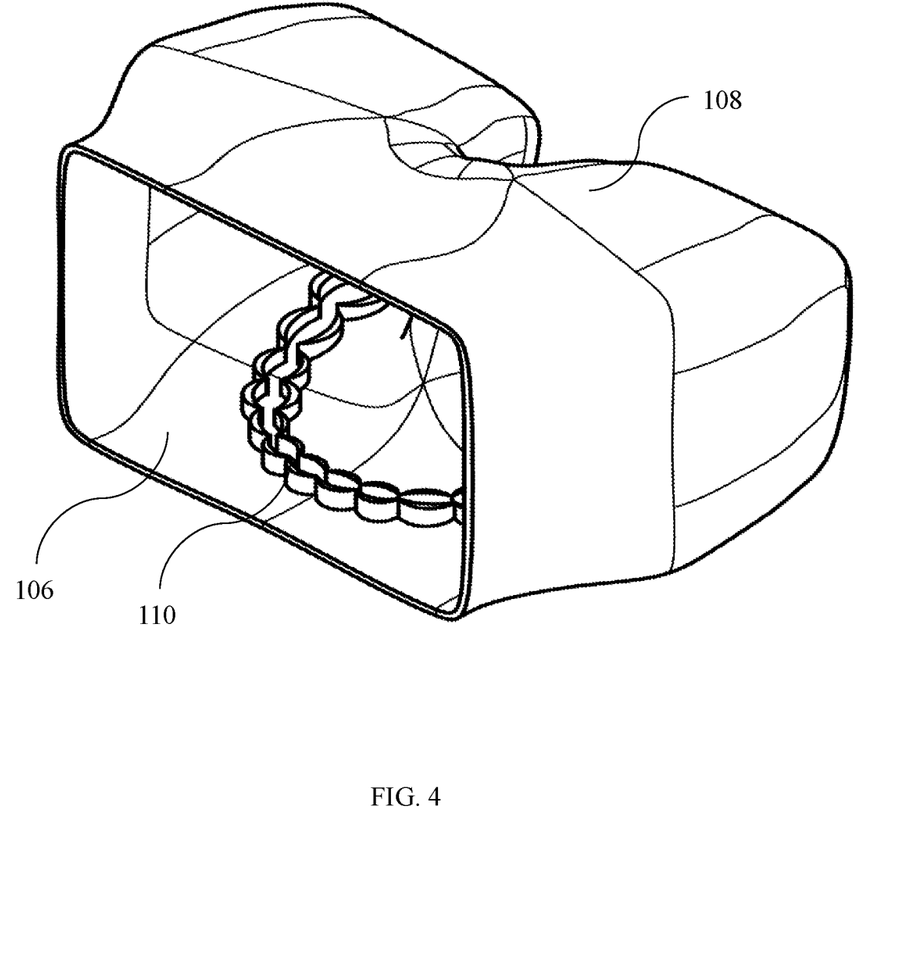
FIG. 4 is a perspective-view of the exemplary oropharyngeal dam inside the patient's mouth, illustrating a sheet and an occlusal barrier, in accordance with an embodiment of the present disclosure.

FIG. 4 is a perspective-view of the exemplary oropharyngeal dam 100 inside the patient's mouth, illustrating an exemplary sheet 104 and an occlusal barrier 110, in accordance with an embodiment of the present disclosure. The sheet 104 further comprises the intra-oral sheet 106 and the extra oral sheet 108. The intra-oral sheet 106 is positioned facing the oral tissues and the extra oral sheet 108 is positioned facing outside the mouth.

Further, the exemplary oropharyngeal dam 100 comprises an occlusal barrier 110. The occlusal barrier 110 can also be referred to as an occlusal indentation slot 110. The occlusal barrier 110 is designed to stretch and accommodate the respective tooth. Moreover, the occlusal barrier 110 aids in securing to the cervical region without requiring additional clamps.

Figure 5:
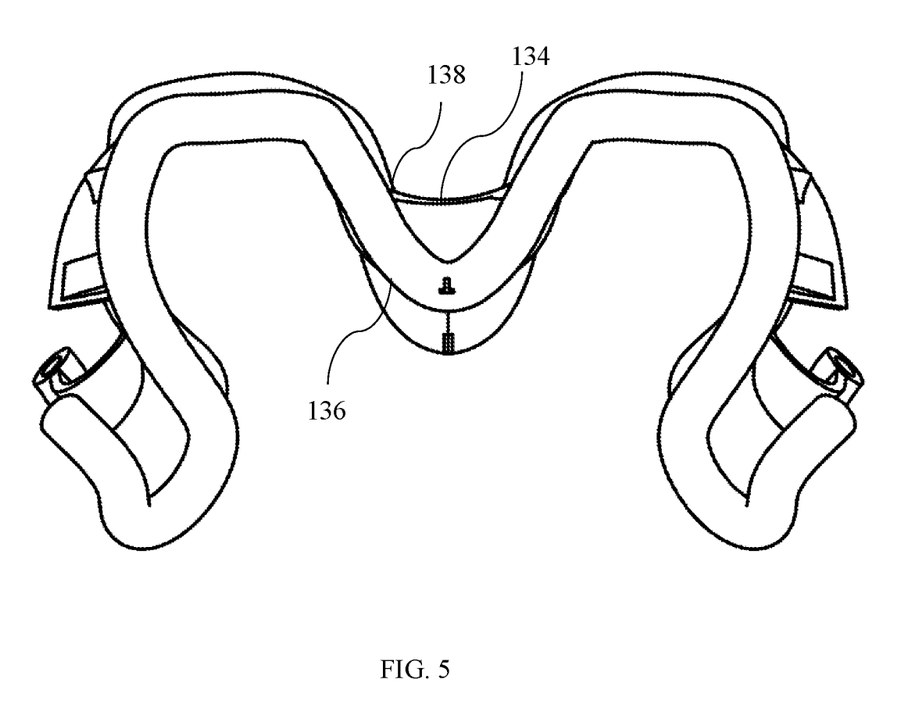
FIG. 5 is a perspective view of the exemplary oropharyngeal dam inside the patient's mouth, illustrating a throat shield, in accordance with an embodiment of the present disclosure.

FIG. 5 is a perspective-view of the exemplary oropharyngeal dam 100 inside the patient's mouth, illustrating a tongue protector 122, in accordance with an embodiment of the present disclosure. The tongue protector 122 is made up of two layers. The first layer is positioned toward the mouth forming the outer sheet 136. The outer sheet 136 facing outwards towards the mouth comprises a set of perforations. The set of perforations collects aerosols formed during the dental procedure and evacuates the collected aerosols via the one or more suction vents 130. The second layer is positioned toward the throat forming the inner sheet 138. The inner sheet 138 acts as a barrier that prevents mix up of patient's respiratory droplets with the aerosol formed during dental procedure and also prevent accidental aspiration of any instruments, debris.

Figure 6:
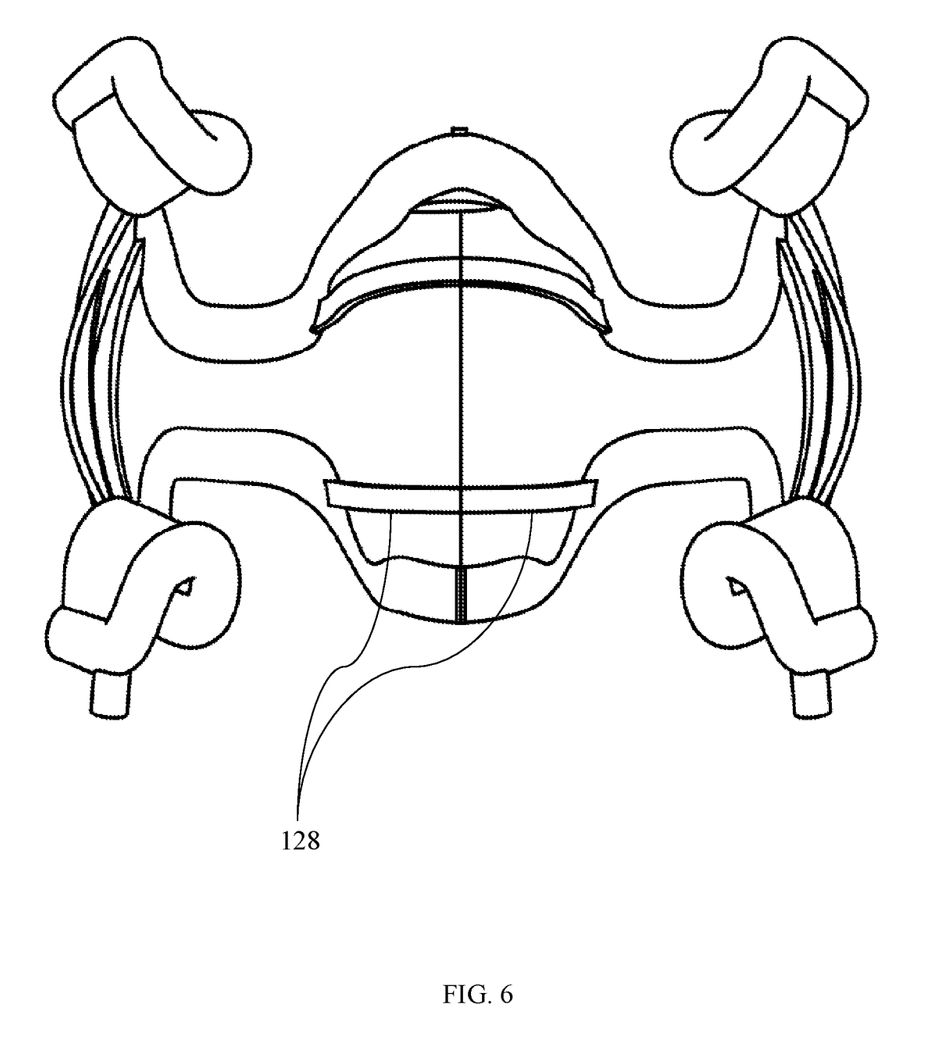
FIG. 6 is a perspective view of the exemplary oropharyngeal dam inside the patient's mouth, illustrating a tongue-protecting sheet, in accordance with an embodiment of the present disclosure.

FIG. 6 is a perspective-view of the exemplary oropharyngeal dam inside the patient's mouth, illustrating a tongue-protecting sheet 128, in accordance with an embodiment of the present disclosure. The tongue-protecting sheet 128 is positioned at the front side/oral side of the throat shield 134. The tongue protecting sheet 128 prevents injury of the tongue by rotary and sharp instruments such as burs blades and the like. Additionally, the protecting sheet 128 prevents accidental swallowing of small dental components used during the dental procedure.

Figure 7:
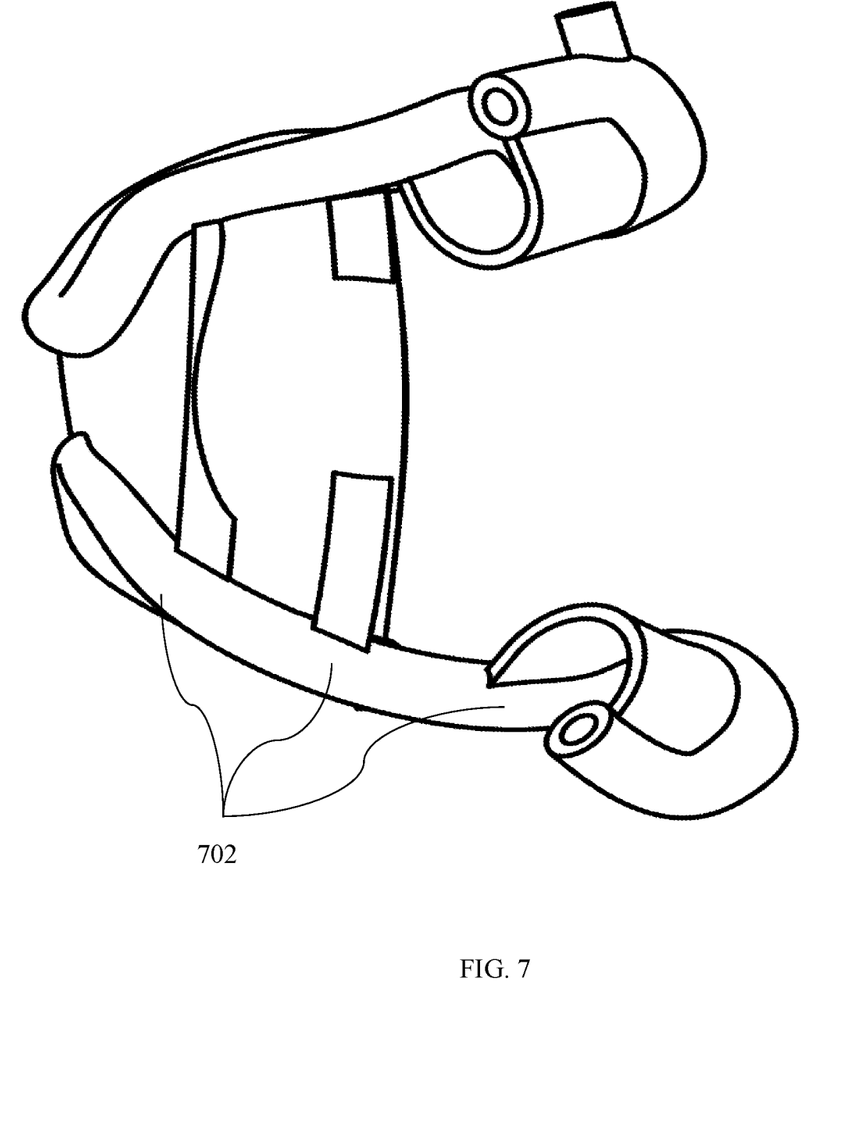
FIG. 7 is a perspective view of the exemplary oropharyngeal dam inside the patient's mouth, illustrating one or more anti-retraction valves, in accordance with an embodiment of the present disclosure.

FIG. 7 is a perspective-view of the exemplary oropharyngeal dam 100 inside the patient's mouth, illustrating one or more anti-retraction valves 702, in accordance with an embodiment of the present disclosure. The one or more suction vents 130 and the one or more external outlets 132 include one or more anti-retraction valves 702 to prevent backflow and cross-contamination. The one or more anti-retraction valves 702 prevent backflow of saliva, water, and debris.

Figure 8:
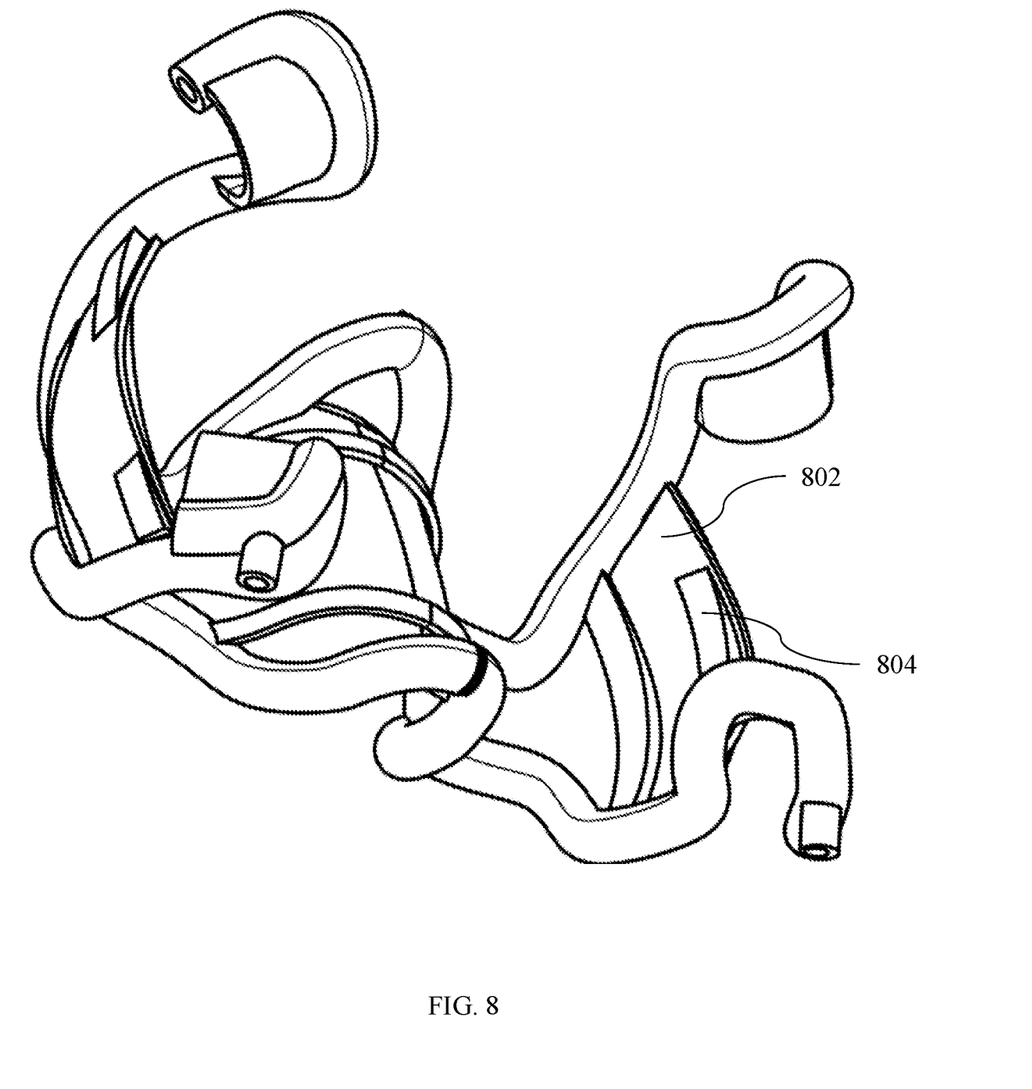
FIG. 8 is a perspective view of the exemplary oropharyngeal dam inside the patient's mouth, illustrating the positioning of flexible mirrors and illuminating devices, in accordance with an embodiment of the present disclosure.

FIG. 8 is a perspective-view of the exemplary oropharyngeal dam 100 inside the patient's mouth, illustrating the positioning of flexible mirrors 802 and illuminating devices 804, in accordance with an embodiment of the present disclosure. The illuminating device 804 can be attached to the inner surface of the cheek retractors 112. The flexible mirrors 802 can be curved and flexible in nature. The flexible mirrors 802 can be inserted or placed in the inner slot of the cheek retractor 112. The flexible mirrors 802 enhance light inside the mouth and also facilitate indirect vision while operating the upper jaw.

Figure 9:
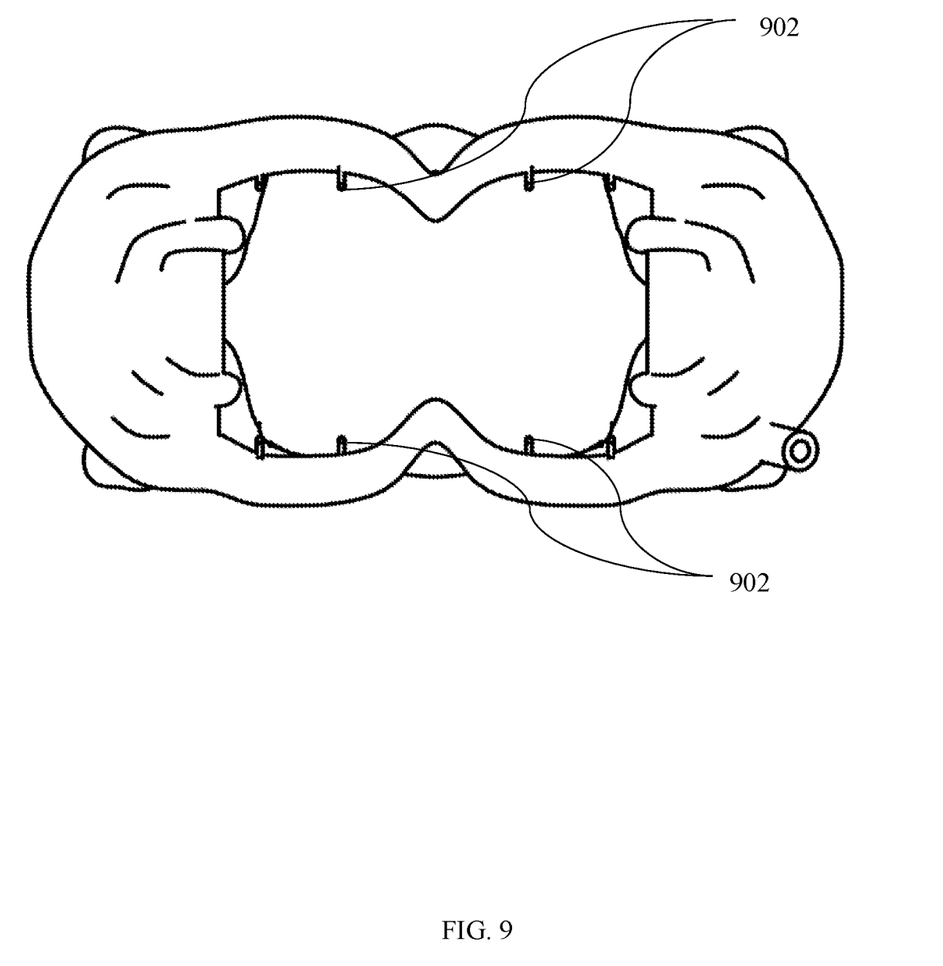
FIG. 9 is a perspective view of the exemplary oropharyngeal dam inside the patient's mouth, illustrating a set of attachment studs, in accordance with an embodiment of the present disclosure.

FIG. 9 is a perspective-view of the exemplary oropharyngeal dam 100 inside the patient's mouth, illustrating a set of attachment studs 902, in accordance with an embodiment of the present disclosure. The extra oral frame 142 includes a set of attachment studs 902 that aid in retaining the sheet 104 to the frame 102.

Various embodiments of the present disclosure provide the oropharyngeal dam 100 for facilitating the safe and efficient dental treatment. In an embodiment of the present disclosure, the oropharyngeal dam 100 provides the functionality of tongue protection, tooth isolation, saliva evacuation, soft tissue retraction, bite block, minimal back splatter of aerosols and the like. Thereby, obviating need of multiple devices for performing different functionalities in mouth. Thus, the oropharyngeal dam 100 is a single multi-functional device. Further, the oropharyngeal dam 100 minimizes cross contamination and enhances safety by formatting a a throat barrier and minimize the mix up of the respiratory droplets with dental drill water. Furthermore, the oropharyngeal dam 100 manages oral and pharyngeal secretions at root source by continuous evacuation of fluids from the oral cavity. The oropharyngeal dam 100 also acts as a throat shield 134 and prevents ingestion of tiny materials and instruments used during the dental procedure. The oropharyngeal dam 100 enhances efficiency of dental treatment by isolating the working area, providing dentist direct access to operating site or tooth, retracting the cheeks & lips, protecting the tongue, enhancing accessibility and visibility in the operating area, illuminating the oral cavity and allowing the patient to keep the mouth open in a comfortable position by supporting the mouth in the opened position. Thus, the oropharyngeal dam 100 increases efficiency of treatment and decreases treatment time. Further, the oropharyngeal dam 100 is reusable and economic to use. The oropharyngeal dam 100 acts as a throat barrier, like intra oral mask, to prevent patient's respiratory droplets from mixing with the dental drill water. The oropharyngeal dam 100 minimizes bioaerosol formation and constantly evacuates the oral fluids and the aerosols. Furthermore, there is minimal back splatter from the oropharyngeal dam 100 and minimal steps in use of the oropharyngeal dam 100. The oropharyngeal dam 100 provides all the functions needed to perform any basic dental procedure safely and efficiently. Each of the functionality has been given a specific form to work in harmony with the others. The oropharyngeal dam 100 has a simplified design and is not technique sensitive, hence any dental health care worker can use it in any part of the world to deliver safe dental treatment for any procedure without any fear of disease transmission.

Further, the oropharyngeal dam 100 creates a barrier in the oral cavity, minimizes the formation of bioaerosols, minimizes aerosol contamination of the patient, dental personnel and workspace, provides for constant evacuation of oral fluids and aerosols, increases safety, comfort of the patient and operator efficiency during the dental procedure, easily visualize the operating area, enhances visibility, and access to the working site. In an embodiment of the present disclosure, the oropharyngeal dam 100 forms a throat barrier and minimizes formation of bio-aerosols by trapping the respiratory droplets and continuously evacuating oral fluids from the oral cavity to avoid contamination of patient, dental personnel and workspace. The oropharyngeal dam 100 traps the exhaled respiratory droplets before entering the oral and nasal cavity, hence reducing the risk of formation of bio-aerosols and reduces cross contamination. Also, the oropharyngeal dam 100 provides an easy to operate oral device that is portable and can be used by any dental health worker in rural and urban areas with minimal training. In an embodiment of the present disclosure, the oropharyngeal dam 100 provides for creation of an anatomically contoured frame with inbuilt evacuation and illumination system. The barrier is designed in a fashion to create minimal back splatter, a universally usable self-retaining sheet that can retract the cheek as well as lips and yet not get dislodged during function. Furthermore, the oropharyngeal dam 100 minimizes assembly time, back splatter of aerosols, need for dental assistant and reduces exposure to additional manpower. Thus, the oropharyngeal dam 100 is easy to use, portable, reusable, reduces medical waste and treatment costs. The oropharyngeal dam 100 is also autoclavable, reduces discomfort and extra costs of Personal Protective Equipment (PPE). Further, the oropharyngeal dam 100 is useful for all the aerosol generating and non-aerosol based dental procedures, compatible with most rotary dental devices, doesn't require additional electricity & clinical workspace and may be used along with pre-existing dental chair facilities. The oropharyngeal dam 100 provides a comprehensive solution that can be used by any dental health care professionals, even in rural or urban setups. Further, the oropharyngeal dam 100 minimizes disease transmission in dental settings which the most crucial yet often overlooked parameter. Thus, the oropharyngeal dam 100 increases operator efficiency and patient comfort while reducing treatment time, as well as operator and patient fatigue. In an embodiment of the present disclosure, the oropharyngeal dam 100 enhances accessibility and visibility by convenient retraction of cheeks, lips and tongue of the operating area thereby reducing the treatment time and reducing patient exposure time. The oropharyngeal dam 100 enhances the illumination and visibility during the dental procedure by the use flexible mirrors 802, LED and similar illumination devices 804.

Furthermore, the oropharyngeal dam 100 focuses to overcome the existing drawbacks of rubber dam which is a gold standard device. The oropharyngeal dam 100 is designed, such that there is a minimal back splatter of aerosols, required minimal steps in assembly yet could provide maximum functions to aid the clinician during the procedure and be comfortable to the patient as well. The oropharyngeal dam 100 provides all the functions needed to perform any basic dental procedure safely and efficiently. For example, the oropharyngeal dam 100 may be use in multiple dental procedures, such as oral examination and diagnosis, use in public health centres, restorative procedures, prosthodontic procedures, endodontic procedures, aesthetic treatments, Light Amplification by Stimulated Emission of Radiation (LASER) based dental services, may be used along with magnification devices, intra oral imaging, documentation and photography in dental practice, radiation protector, treatment of paediatric and geriatric patients, oral tissue biopsy and oral specimens, dental procedures involving LASER, air abrasion, sonics, ultrasonics, and 2D and 3D imaging, dental bleaching, periodontic procedures, dental implants, dental photography, dental surgeries, orthodontic procedures. Thus, the design and working principle of the oropharyngeal dam 100 is simple, efficient and clinician and patient friendly.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, order of processes described herein may be changed and are not limited to the manner described herein. Moreover, the actions of any flow diagram need not be implemented in the order shown; nor do all of the acts need to be necessarily performed. Also, those acts that are not dependent on other acts may be performed in parallel with the other acts. The scope of embodiments is by no means limited by these specific examples.

We claim:

1. An oropharyngeal dam for facilitating a safe and efficient dental treatment, the oropharyngeal dam comprising:
   a pair of cheek retractors located between a set of lip retractors, wherein each of the pair of cheek retractors comprises:
      an upper retractor component configured to adapt to soft tissues of a buccal vestibule of an upper back teeth;
      a lower retractor component configured to adapt to a buccal vestibule of a lower back teeth; and
      a cheek retracting sheet extending between the upper retractor component and the lower retractor component, wherein the upper retractor component, the lower retractor component, the cheek retracting sheet, and the set of lip retractors are collectively configured to retract cheeks of a patient;
   a tongue protector located between the pair of cheek retractors, wherein the tongue protector comprises:
      an upper protector component configured to adapt to a palate of mouth;
      a lower protector component configured to adapt to soft tissues of a lower lingual vestibule; and
      a tongue protecting sheet extending between the upper protector component and the lower protector component, wherein the upper protector component, the lower protector component and the tongue protecting sheet are collectively configured to shield and retract a tongue of the patient;
   the set of lip retractors adjoined with edges of the pair of cheek retractors, wherein the set of lip retractors are configured to aid lip retraction when pulled outside the mouth and on closing the mouth; and
   a throat shield located between the upper protector component and the lower protector component, wherein the throat shield has a curved structure, and wherein the throat shield is a double sheet barrier comprising:
      an outer sheet, wherein the outer sheet facing outwards towards the mouth comprises a set of perforations, wherein the set of perforations collects aerosols formed during the dental procedure and evacuates the collected aerosols via one or more suction vents, and wherein the set of perforations are connected to the one or more suction vents present on the lower protector component;
      an inner sheet, wherein the inner sheet facing towards throat of the patient forms a mechanical barrier to prevent bioaerosol transmission and aspiration of materials used during a dental procedure; and
      one or more flexible straps affixed on the throat shield to hold one or more intraoral radiographs during a dental procedure.

2. The oropharyngeal dam as claimed in claim 1, wherein the lower protector component comprises one or more suction vents configured to aid in suction and evacuation of saliva, oral fluids and bioaerosols formed during a dental procedure, and wherein the one or more suction vents are connected to one or more external outlets to perform the evacuation.

3. The oropharyngeal dam as claimed in claim 2, wherein the one or more suction vents and the one or more external outlets comprise one or more anti-retraction valves to prevent backflow and cross contamination.

4. The oropharyngeal dam as claimed in claim 1, further comprising a pair of bite blocks located between the pair of cheek retractors and the tongue protector, wherein the pair of bite blocks are configured to keep the mouth open in a comfortable and static position throughout the dental procedure.

5. The oropharyngeal dam as claimed in claim 1, further comprises one or more illuminating devices, wherein the one or more illuminating devices comprise but are not limited to one or more Light Emitting Diodes LEDs, fiber optics, and fluorescent dyes that can be attached to the pair of cheek retractors.

6. The oropharyngeal dam as claimed in claim 1, wherein the upper retractor component, the lower retractor component, the upper protector component, and the lower protector component have a tubular structure.

7. The oropharyngeal dam as claimed in claim 1, further comprises visualizing aids such as but not limited to a flexible mirror, intraoral cameras, scanners, sensors, and diagnostic aids that can be placed within the pair of cheek retractors via the set of straps.

8. The oropharyngeal dam as claimed in claim 1, further comprises a set of attachment studs configured to retain a sheet to a frame, enabling single to multiple teeth isolation.

* * * * *